United States Patent [19]
Imaizumi et al.

[11] 4,180,688
[45] Dec. 25, 1979

[54] METHOD FOR CONTINUOUSLY PRODUCING TERT-BUTYL ALCOHOL

[75] Inventors: Masao Imaizumi, Tokyo; Mitsuo Yasuda, Kawasaki; Ko Sakata, Tokyo; Noboru Hirano, Yokohama, all of Japan

[73] Assignee: Nippon Oil Co., Ltd., Tokyo, Japan

[21] Appl. No.: 928,294

[22] Filed: Jul. 26, 1978

[30] Foreign Application Priority Data

Jul. 29, 1977 [JP] Japan ................................ 52/91092
Aug. 8, 1977 [JP] Japan ................................ 52/94798
Aug. 10, 1977 [JP] Japan ................................ 52/96232

[51] Int. Cl.² ............................................. C07C 29/04
[52] U.S. Cl. ............................... 568/899; 568/895; 568/898
[58] Field of Search .................... 568/899, 898, 895

[56] References Cited

U.S. PATENT DOCUMENTS

| 2,477,380 | 7/1949 | Kreps et al. | 568/899 |
| 4,087,471 | 5/1978 | Powman et al. | 568/899 |

*Primary Examiner*—Joseph E. Evans
*Attorney, Agent, or Firm*—Ostrolenk, Faber, Gerb & Soffen

[57] ABSTRACT

A continuous method for producing tert-butyl alcohol from water and isobutylene in the presence of a strongly acidic cation exchange resin as a catalyst is characterized by: said catalyst particles being filled in a reactor, a liquid isobutylene being continuously brought into contact with water such that said liquid isobutylene is filled in a continuous phase in the gaps between said catalyst particles, and that water streams downwardly along the surface of said catalyst particle and subsequently the reaction mixture being continuously taken out from the reactor. According to the method of this invention, tert-butyl alcohol is obtained in a high yield with little formation of by-products.

10 Claims, 2 Drawing Figures

METHOD FOR CONTINUOUSLY PRODUCING TERT-BUTYL ALCOHOL

BACKGROUND OF THE INVENTION

This invention relates to a process for continuously producing in a high yield tert-butyl alcohol (abbreviated as "TBA" hereinunder) from isobutylenes and water by using a strongly acidic cation exchange resin as a catalyst. In particular, this invention is concerned with a process for continuously producing TBA in a high yield without the addition of a third substance such as reaction aiding agents.

It has been well known heretofore to produce TBA by hydrating isobutylenes with use of sulfuric acid having a variety of concentrations. Although the method produces TBA in a comparatively higher yield, it has such defects as producing an isobutylene polymer as a by-product, inability to maintain every part of the equipment safe for a long period due to the use of corrosive sulfuric acid and required treating of waste sulfuric acid.

A direct hydration method of isobutylenes employing phosphoric acid as a catalyst has also been known, however, it requires high temperature and pressure conditions, and the yield of TBA is low.

Further, as to the synthesis of TBA by direct hydration with use of a cation exchange resin catalyst, many methods have been proposed. For example, in Industrial and Engineering Chemistry, vol. 53, No. 3, pp. 209–211, a method in which isobutylene is continuously hydrated by using an ion exchange resin catalyst is disclosed, however, the rate of conversion of isobutylene is about 30% at the highest. In fact, water and isobutylene form a heterogeneous system, and it is difficult to attain an effective reaction between them by merely bringing isobutylene into contact with water in the presence of said catalyst. This fact is also clear from the description of specifications of Japanese Patent Laid-Open Publications Nos. 50-32116, 50-126603, 50-137906 and 51-59802, etc. In order to eliminate the defect, a number of other methods such as adding organic acids in the reaction system as a reaction aiding agent (Japanese Patent Laid-Open Publication Nos. 50-32116 and 50-126603), adding alcohols (Japanese Patent Laid-Open Publication No. 50-137906) and using polar solvents such as ethyl Cellosolve and dioxane and further using emulsifiers, if necessary (Japanese Patent Laid-Open Publication No. 51-59802), have been studied by a number of those skilled in the art heretofore. However, all these methods of add reaction aiding agents have many inconveniences including the addition of a third substance itself, and separating and recovering the reaction aiding agents and separating TBA from the water layer containing them.

Further, a method for hydrating isobutylene by using an ion exchange resin in the state of a suspension is known (Japanese Patent Publication No. 40-2408). The method comprises taking isobutylene, water and a catalyst in a reactor, mixing and stirring to form a suspension thereof, separating the reaction mixture from the reactor into a water layer and an oil layer and recycling of the water layer containing the catalyst in suspension to the reactor. On the one hand, the method may have an advantage in its own way, however, it has defects in that the stirring necessary for keeping the catalyst in a suspension inevitably produces wear and breakdown of the catalyst, and in that at the same time a troublesome operation in which a liquid including the suspended catalyst is treated by recycling is required. Accordingly, in fact, the method is difficult to be performed on an industrial scale.

In particular, when a strongly acidic cation exchange resin such as is employed in this invention is used as a catalyst, the wear and breakdown of the catalyst are further remarkable because the mechanical strength of the resin is weak due to a number of micro-porous structures or cells in the interior thereof. Further, when the catalyst according to this invention is employed in the method in which reaction aiding agents such as an organic acid, alcohol, ethyl Cellosolve, dioxane, surface active agent, etc. are added and reacted in the reaction system, the swelling and deformation of the resin frame resulting from the polar groups of the reaction aiding agent are remarkable, and catalyst life is largely restricted. Therefore, it is very difficult to perform commercially these methods with use of the strongly acidic cation exchange resin having a high catalytic activity of this invention.

As a result of hard studies of various methods for continuously producing TBA in order to remove the defects of the methods heretofore known, the inventors have found the fact that TBA is obtained very effectively by bringing water into contact with isobutylenes, which originally form non-homogeneous or heterogeneous mixtures with the former, by the prescribed method on the surfaces of the specific strongly acidic cation exchange resin catalyst particles and have completed this invention.

SUMMARY OF THE INVENTION

This invention broadly relates to a method to produce TBA by reacting isobutylenes with water in the presence of a strongly acidic cation exchange resin catalyst and more particularly relates to a novel continuous production method of TBA which is characterized by; said catalyst particles being filled in a reactor, a liquid isobutylene being continuously brought into contact with water at a temperature of 50° to 150° C. such that said liquid isobutylene is in a continuous phase in the gaps between said catalyst particles filled and that water flows down along the surfaces of said catalyst particles at an average linear velocity of 1.0 m/hr or more (based on empty vessel) and subsequently the reaction product being continuously taking out from the reactor. This invention is further concerned with another method to produce TBA by reacting isobutylenes with water in the presence of a strongly acidic cation exchange resin catalyst, which is a continuous production method of TBA characterized by; a strongly acidic cation exchange resin catalyst having a surface area of 0.2–120 m$^2$/g, a porosity of 0.03 ml/ml or more, an exchange capacity of 1.0 meq/g or more and a particle size of 0.1–5 mm in dryness thereof being filled in a reactor, a liquid isobutylene being continuously brought into contact with water at a temperature of 50° to 150° C. under the condition that said liquid isobutylene is filled in a continuous phase in the gaps between said catalyst particles and that water flows down along the surfaces of said catalyst particles at an average linear velocity of 1.0 m or more/hr (based on the empty vessel or reactor) and subsequently the reaction product being continuously taking out from the reactor.

Accordingly, it is an object of this invention to provide a method for continuously producing TBA from water and isobutylenes in a high yield by using a strongly acidic cation exchange resin as a catalyst.

Another object of this invention is to provide a continuous production method of TBA in a high yield without adding a third substance, for example, reaction-aiding agents such as an organic acid, alcohol, ethyl cellosolve, dioxane and surface active agent, etc.

A further object of this invention is to provide a method for continuously producing TBA on a commercial scale without using corrosive and detrimental sulfuric acid.

DESCRIPTION OF THE PREFERRED EMBODIMENT

Figure 1:
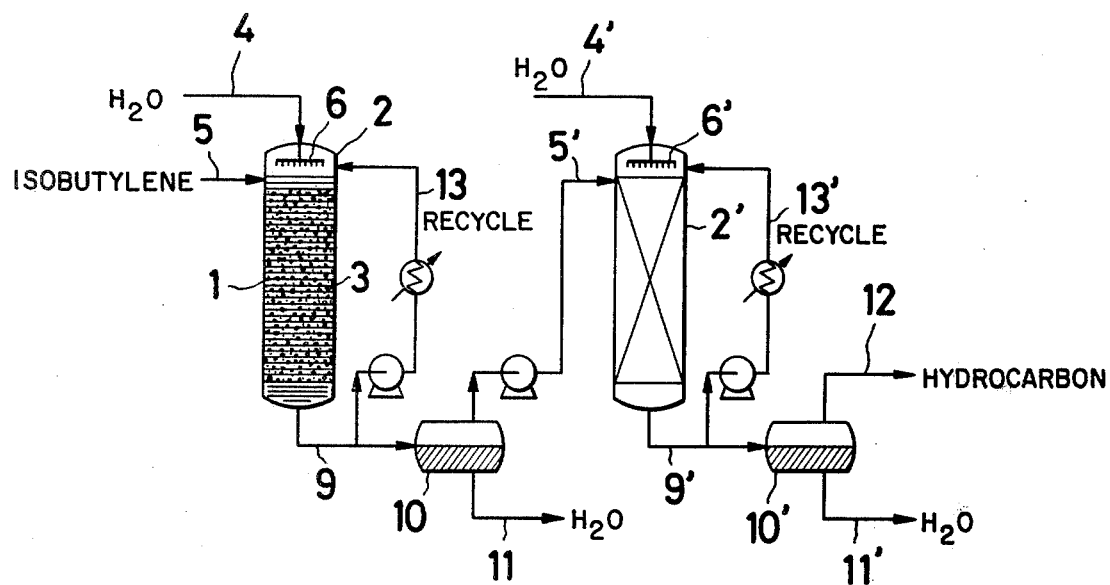
FIG. 1 is a schematic flow diagram illustrating an example of the method according to this invention.

This invention relates to a method for continuously producing TBA in a high yield by contacting isobutylenes with water in the presence of a strongly acidic cation exchange resin as a catalyst. In particular, this invention relates to a continuous method for producing TBA in a high yield without adding a third substance such as a reaction-aiding agent.

This invention will be described more in detail hereinunder.

As the isobutylenes referred to in this invention, isobutylene-containing hydrocarbons such as isobutylene itself, a mixture of isobutylene, butenes and/or butanes and a mixture of isobutylene and other inactive hydrocarbons can be employed. For the industrial purpose, $C_4$ hydrocarbon mixture obtained from a thermal cracking, catalytic and steam cracking of petroleum, preferably those from which butadiene was removed are used. The concentration of isobutylene in these mixtures is generally less than 80% and is generally in the range of 20–50%. Particularly, this invention provides one a method to synthesize TBA effectively from the above-mentioned isobutylene-containing hydrocarbons.

The strongly acidic cation exchange resin referred to in this invention is a cation exchange resin having a strong acidity, of which a styrene sulfonic acid type resin and phenol sulfonic acid type resin are typical. The styrene sulfonic acid type resin is obtained by sulfonating a resin obtained by copolymerizing styrene and a multi-unsaturated compound such as divinylbenzene, and a sulfonic acid group ($—SO_3H$) is introduced into the bridged copolymer.

The phenol sulfonic acid type resin is a resin generally obtained by introducing—$SO_3H$ groups into a condensation product of phenol and formaldehyde.

According to this invention, these strongly acidic ion exchange resins are generally used in the form of particles having an average particle size of about 0.1 - about 10 mm, preferably of 0.3–2 mm.

The strongly acidic cation exchange resin employed in this invention is formed from a styrene-divinylbenzene copolymer, and factors representing the ion-exchange capacity, particle size, specific gravity, degree of cross linking, surface area and porosity, etc. properties are especially important. The inventors have found the fact that a strongly acidic cation exchange resin having a surface area, porosity, ion-exchange capacity and particle size belonging to certain specific ranges among these factors is very useful as a catalyst for synthesizing TBA from isobutylene and water.

As to the surface area, it is in the range of 0.2–120 $m^2/g$, preferably 0.4–100 $m^2/g$. For the measurement of the surface area, the cation exchange resin dried in vacuum at 80° C. for 6 hours is employed, and the measurement is carried out by using nitrogen in accordance with the BET's surface area measuring method. When the numerical value is less than 0.2 $m^2/g$, the intended hydration reaction velocity is retarded, and when larger than 120 $m^2/g$, problems of durability and mechanical strength of said resin arise.

With regard to the porosity, it is determined by using mercury in accordance with the method described in Prac. Natl. Acad. Soci., Vol. 7, P., 115 (1921). Resins having a numerical value of 0.03 ml/ml or more thus measured are useful and the one having a numerical value preferably in the range of 0.05–1.0 ml/ml is especially useful. In case the porosity is small, it becomes a defect that retards the intended hydration reaction velocity. Such a resin as is usually named a gel-type one is outside this range of porosity. In this invention, such a type of resin as has the prescribed small pores in the structure thereof is preferably employed.

The strongly acidic cation exchange resin used in this invention has an ion-exchange capacity of 1.0 meq/g or more, preferably of 2.0–6.0 meq/g, a particle size of 0.1–5 mm, and a true specific gravity of 1.0–1.4. The ion-exchange capacity is represented by a milligram equivalent of sulfonic acid group contained in one gram of dry catalyst particles. When it is 1.0 or less, the yield of TBA is reduced.

Further, in case the particle size is 0.1 mm or less, it is not practical for use in a packed fixed-bed, and when it is 5 mm or more, it reduces the catalytic activity of the resin. It is preferable that the strongly acidic cation exchange resin of this invention has a divinylbenzene content in the resin structure (degree of cross linking) in the range of 1–15% together with these properties.

The strongly acidic cation exchange resin having these characteristic properties of this invention is produced by sulfonating a high molecular weight polymer which is obtained, for example, in the copolymerization of styrene and divinylbenzene, by carrying out the polymerization reaction with use of a solvent that is a good solvent for monomers but is poor in the property to swell polymers, for example, tert-amyl alcohol, sec-butyl alcohol and isooctane, etc.

This invention provides one a method for continuously producing TBA in a very high yield by using these specific strongly acidic cation exchange resin as a catalyst to bring isobutylenes into contact with water in the prescribed method on the surfaces of said catalyst particle.

This invention will be further explained hereinunder in accordance with the accompanying drawings.

In FIG. 1, catalyst particles 1 are packed in reactor 2 in the state of a fixed bed. The reactor is usually length longitudinally and has a wire gauze or porous plate at the bottom on which the particulate catalyst is packed. In reaction zone 3, that is, a zone which the catalyst particles within the reactor fill, liquid isobutylene is filled up between the gaps of the catalyst particles.

Water, one of the reactants is continuously fed in the liquid state at the upper area of the reactor through distributor 6.

Figure 2:
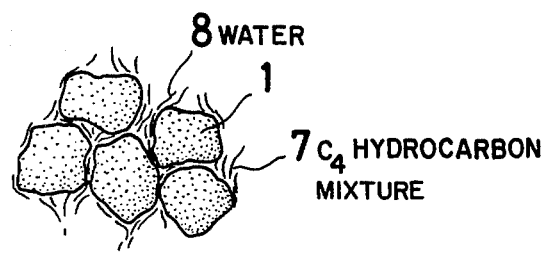
FIG. 2 is a partially enlarged diagram showing the contact state of isobutylene and catlyst particles employed in this invention.

In what a manner isobutylene and the catalyst particles are contacted with one another is clearly shown in FIG. 2. In FIG. 2, the catalyst particle is represented by numeral 1, and isobutylene 7 is filled in the continuous phase and liquid state in the system. Water is represented by numeral 8 and flows down along the surfaces of the catalyst particles. It is not always necessary that all of the surfaces of the catalyst particles are covered with water flowing down, however, the wider the covered surface area is, the more preferable it is.

The flowing of water downward is due to gravity and that the specific gravity of water is larger than that of isobutylene forming the continuous phase.

Isobutylene is dissolved in water by penetrating through a film of water stream covering the catalyst particle, thereby to attain the catalytic reaction of water and isobutylene on the catalyst surface.

When the catalytic reaction is carried out in this manner, TBA is formed in quite a high yield, and a isobutylene polymer by-product is hardly formed.

The reason that such an excellent synthetic effect is attained is not clear, however, it seems probable that a specific catalytic way on the catalyst surface and affinity for and condition of adsorption in the catalyst surface of isobutylene and water, etc. act upon the formation of TBA in a high yield.

According to this invention, isobutylene forming a continuous phase is continuously fed through line 5 in the liquid state, and the reaction mixture brought into contact as described above is drawn out via line 9. By the feed of isobutylene, while the isobutylene forming a continuous phase further forms a continuous phase as a whole, some part of isobutylene transfers downwardly in the reactor.

In FIG. 1, a case wherein isobutylene in a continuous phase continuously goes down from the upper part of the reactor to the lower part thereof, as described above, is shown. In this invention, however, such a method as comprises feeding isobutylene at the lower part of the reactor, transferring it upwardly forming a continuous phase as a whole and taking it out at the upper part of the reactor (not shown in the figure) may also be employed.

In order to perform effectively such a catalytic method as this invention, for example, the following means are taken.

The reactor is filled with liquid hydrocarbon (isobutylene-containing hydrocarbons or inactive hydrocarbons), isobutylene is supplied through line 5, and water through line 4, and then the temperature is gradually increased to initiate the reaction. Further, although isobutylene and water are supplied through lines 5 and 4 respectively, in the initial stage, a method to draw out more water through line 9, to fill isobutylene in the reactor and to raise the temperature may also be taken.

In this invention, the cation exchange resin employed is preferably used by fully wetting with water initially. The wetting with water is attained by immersing said cation exchange resin in a large amount of water usually at a temperature of 0°–100° C., for example, for from 1 minute to 24 hours.

In this invention, when the cation exchange resin fully previously wet with water is employed, side formation of secondary reaction products, especially of isobutylene polymers is inhibited, and further the degradation of the activity of catalyst is remarkably decreased.

When the cation exchange resin fully wet with water initially is used as described above, the following means are preferably taken: said dry resin is filled in said reactor vessel, water is fed therein to be contacted with said resin, after the contact water is exhausted and then isobutylene is filled in the reactor in the manner as described before.

In this invention, the reaction temperature is in the range of 50°–150° C., preferably of 60°–100° C. When it is below 50° C., the reaction velocity becomes slow, and TBA cannot effectively be formed. In contrast, if it is over 150° C., such by-products as isobutylene dimer, isobutylene trimer and sec-butyl alcohol, etc. are greatly formed, and at the same time the catalyst is also greatly deteriorated.

According to this invention, there is no particular limitation with regard to the reaction pressure. Any pressure at which isobutylene or isobutylene-containing hydrocarbons and water form a liquid state at the reaction temperatures above may be taken. Conventionally, a pressure ranging from 2 to 50 $Kg/cm^2$ G, preferably from 5 to 40 $Kg/cm^2$ G, is used. Further, in this invention, water is fed at an average linear velocity of 1.0 m/hr or more, preferably of 1.0–30 m/hr. more preferably of 1.5–20 m/hr, based on the empty vessel of the reactor.

In order to maintain said linear velocity of water, besides the continuous feeding of a prescribed quantity of water, it is possible to employ a recycle method and supply a portion of unreacted water effluent from the reactor. When the average linear velocity is 1.0 m/hr or less, the conversion rate of isobutylene into TBA becomes low, and the undesirable polymerization of butenes is liable to be promoted.

According to this invention, isobutylenes are fed at an average linear velocity based on the empty vessel of the reactor of 0.2–50 m/hr, preferably 1.0 m/hr or more, for example, 1–30 m/hr.

The feeding quantity of water and isobutylenes represented by their LHSV relative to the catalyst is each 0.1–5.0 $hr^{-1}$, preferably 0.2–4 $hr^{-1}$, most preferably 0.3–1.5 $hr^{-1}$.

When the linear velocity of water based on the empty vessel is 1.0 m/hr or more, for example, 1.0–30 m/hr and cation exchange resins having properties outside the ranges described in this invention are employed as a catalyst, the catalytic activity for hydration reaction becomes small, and therefore a large quantity of the catalyst is required for obtaining a satisfactory catalytic activity, and as a result, the reactor as a whole takes a longitudinally length shape. Owing to these facts, the following inconveniences take place: water becomes hard to flow down along the surface of catalyst particle and shows a tendency that a greater portion of water causes channeling along tube walls, the productivity of TBA is decreased, and the manufacture of a shell and tube type reactor effective for removing reaction heat becomes considerably and technically difficult.

Moreover, when the catalyst according to this invention is used but the specific catalytic method of the reactants and catalyst particles in this invention is not employed, it is difficult for the catalytic reaction of water and isobutylenes on the catalyst surface to proceed uniformly, and an undesirable side reaction is liable to occur owing to the very high activity of catalyst.

Further, when the catalytic reaction is carried out, for example, under conditions of suspension and stirring with use of the specific catalyst of this invention, a severe wear and breakage of the catalyst result.

The reaction mixture catalytically reacted as described above is drawn out through line 9, and TBA is separated and recovered therefrom by conventional methods. In this case, a portion of the reaction mixture taken out through line 9 may be recycled to the reactor through line 13. By such recycling control of temperatures in the reactor and uniform reaction are carried out to make the catalytic reaction more effective.

In this invention, the above catalytic reaction can be preformed in a multiple stage way. In this case (example shown in FIG. 1), the reaction mixture taken out from reactor 2 in the first stage through line 9 is introduced into a settler 10 to be separated into a hydrocarbon phase and water phase. The hydrocarbon phase is lead into the same reactor 2' as that of the first stage through line 5', and the water phase is drawn out at the lower part of settler 10 through line 11 and is transferred to a separating and recovering apparatus such as a distillation or an azeotropic distillation apparatus (not shown in the figure) to recovery TBA. Water is fed at the upper portion of the second stage reactor 2' through line 4' and distributor 6'. In the reactor of the second stage, the same catalytic reaction as that in the first stage reactor is carried out. The reaction product thus formed is drawn out through line 9' and is introduced into settler 10'. In this case, a portion of the reaction mixture is preferably recycled to the reactor through line 13'. The reaction mixture in settler 10' is divided into a hydrocarbon phase and water phase. The divided hydrocarbon phase is taken out through line 12, and the water phase is drawn out through line 11' to separate and recover TBA in the same manner.

In order to explain this invention more concretely, several examples thereof will be shown hereinunder.

EXAMPLE 1

In a cylindrical reactor of 10 cm in diameter and of 15.7 lit. in inside capacity was packed a strongly acidic cation exchange resin (effective diameter 0.45–0.6 mm, ion-exchange capacity 3.5 meq/g) as a catalyst. The catalyst resin was obtained by sulfonating a resin prepared by copolymerizing (divinylbenzene content 12%) styrene and divinylbenzene and fully wet with plenty of water before packing. Water and a liquid isobutylene-containing hydrocarbon was continuously fed in the reactor by a plunger pump. As the liquid isobutylene-containing hydrocarbon, a fraction prepared by extracting butadienes from fractions obtained from a steam cracking of petroleum naphtha was used. The composition is as follows:

| Isobutane | 5.3 wt. % |
|---|---|
| n-Butane | 13.4 wt% |
| trans-Butene-2 | 6.8 wt% |
| Isobutylene | 44.1 wt% |
| Butene-1 | 25.1 wt% |
| cis-Butene-2 | 5.3 wt% |

Prior to the starting of the reaction, the reactor is cooled to 5° C., and the liquid isobutylene-containing hydrocarbon was packed in the reactor to form a continuous phase thereof. After that, the water and isobutylene-containing hydrocarbon each are fed in the reactor at the upper part thereof at a rate of 0.5 lit./hr initially and are gradually increased to reach 16 lit./hr finally. The linear velocity of water at this time is 2 m/hr based on the empty vessel. Water streams downward along the surface of catalyst particles. The temperature of the reactor was 5° C. at the beginning and was gradually raised to reach 90° C. finally. The pressure in the system is kept at a gauge pressure of 30 Kg/cm$^2$ by continuously drawing out the liquid quantity balancing with the feeding quantity.

The hydration reaction was carried out under the above conditions and in non-homogeneous state. The results obtained were as follows;

| TBA formation velocity | 2800 | g/hr |
|---|---|---|
| Isobutylene dimer formation velocity | 1.3 | g/hr |
| sec-Butyl alcohol formation Velocity | 1.8 | g/hr |

As clear from the result, the conversion rate of isobutylene into TBA is as high as about 50%, and the formation of by-products is very small.

EXAMPLE 2

In a cylindrical reactor of 7 cm in diameter and of 4.2 lit. in internal capacity is filled the same strongly acidic cation exchange resin as that in Example 1 (divinylbenzene content, 2%; effective diameter, 0.4–0.6 mm; ion-exchange capacity, 3.3 meq/g) as a catalyst. At the beginning, the ion-exchange resin is fully wet with pure water fed in the reactor at the reaction temperature. Then, the liquid isobutylene-containing hydrocarbon is supplied, and a continuous phase of the isobutylene-containing hydrocarbon is formed in the reactor by mainly discharging water. The liquid isobutylene-containing hydrocarbon used at this time is a fraction obtained by a catalytic cracking of gas oil, and the composition is as follows:

| Isobutane | 41.1 wt % |
|---|---|
| n-Butane | 8.8 wt % |
| trans-Butene-2 | 10.6 wt % |
| Isobutylene | 20.5 wt % |
| Butene-1 | 11.4 wt % |
| cis-Butene-2 | 7.6 wt % |

In the above state, said liquid isobutylene-containing hydrocarbon and water each are fed in the reactor maintained at 90° C. and 20 Kg/cm$^2$ G at the upper part thereof at a velocity of 5 lit./hr. The linear velocity of water at this time is 1.3 m/hr, based on the empty vessel. Water flows down along the surface of catalyst particle. The pressure of the system is kept at 20 Kg/cm$^2$ G by taking out continuously the liquid amount corresponding to the feeding amount therefrom. The reaction products obtained are as follows:

| TBA Formation velocity | 414 | g/hr |
|---|---|---|
| Isobutylene dimer formation velocity | 0.8 | g/hr |
| sec-Butyl alcohol formation velocity | 1.53 | g/hr |

As clear from the results, the conversion rate of isobutylene into TBA is as high as about 51%, and production of by-products is quite little.

EXAMPLE 3

In a shell and tube type reactor having an inside capacity of 15 m$^3$ is filled a sulfonic acid type cation exchange resin (ion-exchange capacity, 2.9 meq/g; particle size, 0.35–1.2 mm) prepared by sulfonation of a styrene-divinylbenzene copolymer as a catalyst. A continuous phase of liquid isobutylene-containing hydrocarbon is formed in the reactor in the manner as described in Example 1. The isobutylene-containing hydrocarbon as a raw material is a hydrocarbon mixture obtained by extracting butadienes from a $C_4$ hydrocarbon mixture obtained by steam cracking of naphtha, and the isobutylene content thereof is 46.4 wt%. The liquid isobutylene-containing hydrocarbon and water are continuously charged into the reactor at the upper part thereof while the temperature of reaction zone is controlled with cooling water. Each of their charging rates is maintained at 8 $m^3$/hr finally, and the reaction temperature is controlled by cooling water so as to be 90° C. The linear velocity of water based on the empty vessel in the stationary state is 10.8 m/hr, and water runs down along the surface of catalyst particle. The reactor pressure is maintained at 20 Kg/$cm^2$ G by continuously drawing out the liquid quantity balancing with the feeding amount of water and isobutylene-containing hydrocarbon.

The reaction is carried out under these conditions described above, and the reaction mixture thus obtained was analyzed. The results were as follows:

| | | |
|---|---|---|
| TBA formation velocity | 1.79 | ton/hr |
| Isobutylene dimer formation velocity | 9.35 | Kg/hr |
| sec-Butyl alcohol formation velocity | 15.6 | Kg/hr |

As clearly seen from the result, the conversion rate of isobutylene into TBA is as high as about 60.8%, and further the production of by-products is quite small.

EXAMPLE 4

The reaction is carried out in accordance with the method described in Example 3, and then the reaction mixture is introduced in a liquefied state into a settler to be divided into a hydrocarbon phase and water phase. The flow rate of the isobutylene-containing hydrocarbon including unreacted isobutylenes from the first reactor is 5.74 $m^3$/hr, and the isobutylene content of said hydrocarbon fraction is 25.3 wt%. This isobutylene-containing hydrocarbon is continuously supplied at the upper part of the second reactor together with freshly supplied water. The supplying velocity of water is 5 $m^3$/hr, and the linear velocity based on the empty vessel is 6.75 m/hr. The second reactor is in the same shape as that of the reactor used in Example 3. The reaction temperature of the second reactor is kept at 85° C., and the pressure is controlled at 20 Kg/$cm^2$ G.

In the above situations, the amount of reaction products obtained from the second reactor and the total of those obtained from the first and second reactors are as follows:

| | | Second reactor | | Total of first and second reactors | |
|---|---|---|---|---|---|
| TBA | Formation velocity | 0.69 | ton/hr | 2.48 | ton/hr |
| Isobutylene dimer | Formation velocity | 7.7 | Kg/hr | 17.05 | Kg/hr |
| sec-Butyl alcohol | Formation velocity | 33.4 | " | 49 | " |
| | velocity | | | | |

COMPARATIVE EXAMPLE 1

In a cylindrical reactor of 10 cm in diameter and of 4.2 lit. in inside capacity is filled the same strongly acidic cation exchange resin as that employed in Example 1. Said ion exchange resin is fully wet with pure water supplied in the reactor at the beginning, and then a liquid isobutylene-containing hydrocarbon is fed in the reactor to form a continuous phase of isobutylene-containing hydrocarbon therein. The liquid isobutylene-containing hydrocarbon used at this time is the same as that obtained by extracting butadienes from fractions obtained by a steam cracking of naphtha. The composition is the same as that of the fraction shown in Example 1.

In the state as described above, the liquid isobutylene-containing hydrocarbon having the same composition as that of the liquid isobutylene-containing one forming a continuous phase and water are continuously fed in the reactor at the upper part thereof at a feeding speed of 2 lit./hr. In this case, the reactor is maintained at 90° C. and 20 Kg/$cm^2$ G, and the linear velocity of water is 0.25 m/hr, based on the empty vessel. The stationary state was attained in 6 hours after the initiation of the reaction, however, the formation of isobutylene polymers was remarkable with the following formation rates because the linear velocity of water was too small.

| | | |
|---|---|---|
| TBA Formation velocity | 211 | g/hr |
| Isobutylene dimer formation velocity | 63 | " |
| Isobutylene trimer formation velocity | 81 | " |
| Isobutylene tetramer formation velocity | 23 | " |
| sec-Butyl alcohol formation velocity | 2.7 | " |

As clear from the results, the production rate of TBA is as low as 28%, and further a large quantity of side-reaction products is formed.

COMPARATIVE EXAMPLE 2

In a cylindrical reactor of 10 cm in diameter and 4.2 lit. in inside capacity is filled the same strongly acidic cation exchange resin as that employed in Example 1. The same isobutylene-containing hydrocarbon as that used in Example 1, which is prepared by extracting butadienes from a fraction obtained by a steam cracking of naphtha, and steam are continuously supplied in the reactor at 100° C. and under the atmospheric pressure. The feeding rate of the isobutylene-containing hydrocarbon is 800 lit./hr (GHSV, 190/hr), and that of steam, 1000 lit/hr (GHSV, 240/hr). The quantity of TBA formed is little, and the formation rates are as follows.

| | | |
|---|---|---|
| TBA formation velocity | 1.33 | g/hr |
| Isobutylene dimer formation velocity | 16.2 | " |
| sec-Butyl alcohol formation velocity | 0.03 | " |

As clear from the above results, when the isobutylene and water are both reacted in vapor state, the formation rate of TBA is so low as not to extend to even 1%, and a great amount of by-products is formed.

EXAMPLE 5

In a cylindrical reactor of 15 cm in diameter and of 38 lit. in inside capacity was packed a strongly acidic cation exchange resin (surface area, 54.1 m$^2$/g; porosity, 0.36 ml/ml; ion-exchange capacity, 3.8 meq/g; degree of cross linking, 13.1%, particle size, 0.2-1.5 mm) as a catalyst. The catalyst resin was obtained by sulfonating a resin prepared by copolymerizing styrene and divinylbenzene and was fully wet with a plenty of water before packing. Prior to the start of the reaction, the reactor was cooled to 5° C., and a liquid isobutylene-containing hydrocarbon was filled in the reactor to form a continuous phase of said hydrocarbon. As an isobutylene-containing hydrocarbon, a fraction prepared by extracting and eliminating butadienes from C$_4$ hydrocarbon fractions obtained by a steam cracking of petroleum naphtha, was employed. The composition was as follows;

| | |
|---|---|
| Isobutane | 7.9 wt% |
| n-Butane | 14.1 wt% |
| trans-Butene-2 | 7.4 wt% |
| Isobutylene | 39.2 wt% |
| Butene-1 | 24.5 wt% |
| cis-Butene-2 | 6.9 wt% |

Then, water and liquid isobutylene-containing hydrocarbon were continuously fed in the reactor at the upper part thereof by a plunger pump. The feeding of each of water and isobutylene-containing hydrocarbon was started at 0.5 lit./hr and increased gradually to and maintain finally at 26 lit./hr. The linear velocity of water at the time was 1.5 m/hr, based on the empty vessel, and water streamed downwardly along the surface of the catalyst particles. The reaction temperature of the reactor was gradually raised from 5° C. to reach 92° C. finally. A quanity of liquid balancing with the feeding amount was drawn out at the lower part of the reactor in order to maintain the pressure in the system at 30 Kg/cm$^2$. G.

Under the conditions described above, the hydration reaction was performed in a non-homogeneous state. The results obtained are as follows;

| | | |
|---|---|---|
| TBA formation velocity | 4640 | g/hr |
| Isobutylene dimer formation velocity | 9.7 | g/hr |
| sec-Butyl alcohol formation velocity | 14.3 | g/hr |

As clear from the result, the conversion rate of isobutylene into TBA was as high as about 57.4%, and the formation of by-products was very small.

EXAMPLE 6

In a shell and tube type reactor having an inside capacity of 15 m$^3$ was filled as a catalyst a strongly acidic cation exchange resin (surface area, 3.4 m$^2$/g; porosity, 0.11 ml/ml; ion-exchange capacity, 3.6 meq/g; particle size, 0.2-1.5 mm) prepared by sulfonating a styrene-divinylbenzene copolymer. In the manner described in Example 5, a continuous phase of liquid isobutylene-containing hydrocarbon was formed in the reactor. The isobutylene-containing hydrocarbon employed as a raw material is a fraction obtained by extracting butadienes from a C$_4$ hydrocarbon mixture prepared by a steam cracking of naphtha, and the isobutylene content was 46.4%. Water and isobutylene were continuously charged into the reactor at the upper portion thereof while the temperature of reaction zone was controlled with cooling water. Each of feeding velocities was maintained at 7.2 m$^3$/hr finally. The reaction temperature was controlled with cooling water so as to be 91° C. The linear velocity of water based on the empty vessel in the stationary state is 9.7 m/hr, and water flows down along the surface of catalyst particles. The reactor pressure was maintained at 20 Kg/cm$^2$. G by continuously drawing out a quanity of liquid corresponding to the feeding amount of water and isobutylene-containing hydrocarbon. The reaction was carried out under the conditions as described above. The following results were obtained by analyzing the reaction mixture formed;

| | | |
|---|---|---|
| TBA formation velocity | 1.50 | ton/hr |
| Isobutylene dimer formation velocity | 7.6 | Kg/hr |
| sec-Butyl alcohol formation velocity | 13.2 | " |

The result clearly shows that the conversion rate of isobutylene into TBA is as high as about 67.0%, and that the amount of by-products formed is very little.

EXAMPLE 7

The reaction is carried out in accordance with the method described in Example 6. After that, the reaction mixture is introduced in a liquefied state into a settler to be divided into a hydrocarbon phase and water phase. The flow rate of isobutylene-containing hydrocarbon including unreacted isobutylene from the first reactor was 5.31 m$^3$/hr, and the isobutylene content of the fraction was 17.3 wt%. The isobutylene-containing hydrocarbon was continuously supplied in the second tower at the upper portion thereof with freshly fed water. The feeding velocity of water is 5.3 m$^3$/hr, and the linear velocity, based on the empty vessel, 7.16 m/hr. The second reactor is in the same shape as that of the reactor used in Example 6. In the second reactor, a continuous phase of isobutylene-containing hydrocarbon has already been formed. The temperature and pressure of the second reactor are controlled at 85° C. and 20 Kg/cm$^2$. G, respectively.

Under the above conditions, the amount of reaction products obtained from the second reactor and the total of those from the first and second reactors are as follows:

| | Second reactor | | Total of first and second reactors | |
|---|---|---|---|---|
| TBA formation velocity | 0.40 | ton/hr | 1.90 | ton/hr |
| Isobutylene dimer formation velocity | 3.8 | Kg/hr | 11.4 | Kg/hr |
| sec-Butyl alcohol formation velocity | 12.2 | " | 25.4 | " |

What is claimed is:
1. In a method of continuously producing tert-butyl alcohol by reacting water with isobutylene in the presence of a strongly acidic cation exchange resin as a catalyst, the improvement which comprises continuously bringing water and liquid C$_4$ hydrocarbon mixture containing 20-50% isobutylene into contact with each other and a bed of said catalyst particles in a reactor at a temperature of 50°-150° C. under conditions such that said liquid $C_4$ hydrocarbon mixture is the continuous phase in the gaps between the catalyst particles in said bed said continuous phase being obtained by filling the reactor with a liquid $C_4$ hydrocarbon mixture and the water flows along the surface of the catalyst particles at an average linear velocity of at least 1.0 m/hr (based on the empty reactor) and continuously withdrawing reaction mixture from the reactor.

2. The method of claim 1, wherein said catalyst has a surface area of 0.2–120 $m^2/g$, a porosity of at least 0.03 ml/ml, an ion-exchange capacity of at least 1.0 meq/g and a particle size of 0.1–5 mm.

3. The method of claim 2, wherein said catalyst has a surface area of 0.4–100 $m^2/g$, a porosity of 0.005–1.0 ml/ml, an ion-exchange capacity of 2.0–6.0 meq/g and a particle size of 0.3–2 mm, wherein said temperature is 60°–100° C. and wherein said average linear velocity is 1–30 m/hr.

4. The method of claim 3, wherein said average linear velocity is 1.5–20 m/hr.

5. The method of claim 3, wherein the reaction pressure is 2–50 $kg/cm^2$ G and wherein the average linear velocity of said liquid $C_4$ hydrocarbon mixture is 0.2–50 m/hr.

6. The method of claim 5, wherein said pressure is 5–50 $kg/cm^2$ G and said liquid $C_4$ hydrocarbon mixture average linear velocity is 1–30 m/hr.

7. The method of claim 1, wherein said strongly acidic cation exchange resin is a sulfonated styrene-divinylbenzene resin.

8. The method of claim 1, wherein said strongly acidic cation-exchange resin is contacted with water prior to the catalytic reaction.

9. The method of claim 1, wherein a portion of the water in the recovered reaction mixture is recycled to said reactor.

10. The method of claim 1, wherein an isobutylene containing fraction from said recovered reaction mixture is, together with water, introduced into a bed of said catalyst particles in a second reactor at a temperature of 50°–150° C. such that said isobutylene containing fraction is the continuous phase in the gaps between the catalyst particles in said bed and the water flows along the surface of said catalyst particles at an average linear velocity of at least 1.0 m/hr (based on the empty reactor) and reaction mixture is continuously withdrawn from said second reactor.

* * * * *